(12) United States Patent
Salehi et al.

(10) Patent No.: US 6,645,251 B2
(45) Date of Patent: Nov. 11, 2003

(54) SURFACES AND PROCESSES FOR WEAR REDUCING IN ORTHOPAEDIC IMPLANTS

(75) Inventors: Abraham Salehi, Bartlett, TN (US); Mark Harbaugh, Germantown, TN (US); Willard L. Sauer, Wernersville, PA (US); Christopher Patrick Carson, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/055,248

(22) Filed: Jan. 22, 2002

(65) Prior Publication Data

US 2002/0161447 A1 Oct. 31, 2002

Related U.S. Application Data

(60) Provisional application No. 60/263,821, filed on Jan. 22, 2001.

(51) Int. Cl.[7] .............................. A61F 2/38; A61F 2/30
(52) U.S. Cl. ............................. 623/20.28; 623/20.29; 623/18.11
(58) Field of Search ..................... 623/20.14, 20.15, 623/20.19, 20.21, 20.28, 20.29, 20.31, 18.11, 20.17

(56) References Cited

U.S. PATENT DOCUMENTS

| | | |
|---|---|---|
| 3,683,421 A | 8/1972 | Martinie |
| 3,864,758 A | 2/1975 | Yakich |
| 4,032,994 A | 7/1977 | Frey |
| 4,571,358 A | 2/1986 | Suh et al. |
| 4,676,799 A | 6/1987 | Legrand |
| 4,731,088 A | 3/1988 | Collier |
| 4,840,631 A | 6/1989 | Mathys |
| 5,197,987 A * | 3/1993 | Koch et al. ................... 623/20 |
| 5,358,530 A * | 10/1994 | Hodorek ...................... 623/20 |
| 5,462,362 A | 10/1995 | Yuhta et al. |
| 5,549,681 A * | 8/1996 | Segmuller et al. ............. 623/18 |
| 5,662,158 A * | 9/1997 | Caldarise .................... 164/456 |
| 5,776,200 A * | 7/1998 | Johnson et al. ............... 623/20 |
| 6,045,581 A * | 4/2000 | Burkinshaw ................. 623/18 |
| 6,414,086 B1 * | 7/2002 | Wang et al. ................ 525/191 |
| 2002/0090154 A1 * | 7/2002 | Murray ....................... 384/192 |

FOREIGN PATENT DOCUMENTS

| | | |
|---|---|---|
| DE | 2139878 | 8/1971 |
| DE | 3343863 C2 | 12/1983 |
| DE | 3741490 | 12/1987 |
| EP | 0084 094 | 11/1982 |
| EP | 0565742 | 4/1992 |
| JP | 6-313430 | 8/1994 |
| WO | WO 95/01139 | 1/1995 |

OTHER PUBLICATIONS

Clarke, et al., "Hip–Simulator Ranking of Polyethylene Wear—Compassions Between Ceramic Heads of Different Sizes," *Acta. Orthop. Scand.*, 67 (2):128–132 (1996).

(List continued on next page.)

*Primary Examiner*—Eduardo C. Robert
*Assistant Examiner*—Anuradha Ramana
(74) *Attorney, Agent, or Firm*—Kilpatrick Stockton LLP; James L. Ewing, IV; Kristin D. Mallatt

(57) ABSTRACT

Artificial implants having reduced area to provide reduced wear are provided. The reduced area is particularly located at areas where greatest wear is exhibited. In a particular embodiment of a mobile bearing knee implant, the area is reduced on the mobile bearing insert underside, where it contacts a tibial component. The reduced area may be any shape of indentations, for example, grooves, dimples, straight patterns, curved patterns, crossing patterns, holes, channels or slots. The indentations may be various sizes, and have been found to be particularly effective if covering about 10% to about 20% of the insert at depths between about 1–2 mm.

21 Claims, 7 Drawing Sheets

OTHER PUBLICATIONS

Nishimura, et al., "Modification of the Frictional Surfaces of Artificial Joints," *ASAIO Journal*, M762 (Jul.–Sep. 1993).

Sauer, et al., "Predicting the Clinical Wear Performance of Orthopaedics Bearing Surfaces," in J.J. Jacobs and T.L. Craig, eds., *Alternative Bearing Surfaces in Total Joint Replacement; ASTM STP 1346* pp. 1–29 (Dec. 1998).

Spector, Myron, "The Smith & Nephew Mobile Bearing Knree," pp. 1–2 (May 11, 1999).

Wang, et al., "Effect of Head/Cup Clearance on the Wear of UHMWPE in Total Hip Replacement," *Trans $24^{th}$ SFB*, San Diego, CA 357 (Apr. 1998).

Whiteside, "Profix Total Knee System," Smith & Nephew, pp. 1–69 (Jan. 1998).

* cited by examiner

UHMWPE wear vs. cycles for conditions C, S, and X (n=1 each) compared to baseline mobile bearing and fixed bearing wear (n=3 each).

A comparison of reduction in wear vs. reduction in backside surface area for each condition.

SURFACES AND PROCESSES FOR WEAR REDUCING IN ORTHOPAEDIC IMPLANTS

This application claims priority to U.S. Provisional Application No. 60/263,821, filed on Jan. 22, 2001, entitled "Surfaces and Processes for Wear Reduction in Orthopaedic Implants," the entire contents of which are hereby incorporated herein by reference.

BACKGROUND OF THE INVENTION

1. Field of the Invention

The present invention relates to devices, structures and processes for reducing friction and wear of orthopaedic implant components, particularly bearing components, and more particularly ultra-high molecular weight polyethylene (UHMWPE) components, by providing certain novel textured or patterned surfaces on such components.

2. Description of Related Art

Orthopaedic implants are becoming increasingly prevalent as millions of patients have been relieved of suffering from joint degenerative diseases and other conditions that affect proper hip, knee, shoulder and other joint function. Total or partial joint replacement procedures involve removal of damaged parts of the relevant joint and replacing them with prosthetic components. During surgery, implant components especially selected to match the patient's needs are located and implanted in the bones forming the joint. In a total joint replacement, it is often the case that a bearing component is interposed between two other components that articulate, or move in a manner that corresponds to relative motion of the bones forming the joint, particularly when the articulating components are formed of metal. For purposes of this document, implant component surfaces disposed against or adjacent to each other in normal operation of the implant are referred to as bearing surfaces. Bearing surfaces may be articulating bearing surfaces, when the two components engage in articulating motion relative to each other, or non-articulating bearing surfaces when they do not engage in articulating motion relative to each other.

A common problem involved with joint replacements is the high wear rates that occur once the components have been implanted. Particularly, mobile bearing components, such as those formed of ultra-high molecular weight polyethylene ("UHMWPE"), present wear rates that are substantially higher than those for corresponding fixed bearing components. This increased wear causes the need for increased replacements and revisions, which are commonly more labor intensive, more expensive, and more traumatic to the surrounding tissue and bone.

Accordingly, there is a great need to reduce the wear that accompanies artificial joints. Such wear occurs in all types of artificial joints, including knee, hip, shoulder, elbow, finger, toe, or spinal systems.

More specifically, the prosthetic components contact one another during all types of forward, backward, and side to-side movements. Some replacement joints, such as knee joints, have a mobile bearing insert located between the components implanted in the tibia (such as a tibial tray attached to a tibial stem) and the components implanted in the femur (such as a condylar component attached to a femoral stem). The insert acts, among other things, to ease and facilitate movement of the components and to retain the knee components in place. Particularly if the knee is reconstructed as a mobile bearing knee, the insert is allowed to rotate and translate with the actual motion of the knee. The insert is not constrained, so that it can move in the anterior-posterior direction and/or the medial-lateral direction, which often creates considerable wear. (Other joints also experience wear due to sliding movement.)

For example, many presentations and articles that address mobile bearing knees note that the wear behavior expected of these joint replacements is similar to that obtained with total hip arthroplasty. Specifically, the wear mechanisms include adhesive and abrasive wear, generating a large number of relatively small (micrometer and submicrometer) polyethylene wear particles. The reduction of wear debris generated by orthopaedic devices is one of the leading issues regarding long term performance of orthopaedic joint prostheses.

Wear debris has been associated with adverse biological responses which can lead to local cell death (osteolysis for bone cells), premature loosening and failure of orthopaedic devices, and subsequent need for revision surgery. The majority of wear debris originates from articulating surface of orthopaedic devices, typically a UHMWPE insert or cup surface that is disposed against a metal or ceramic plate or ball surface in a manner such that the surfaces engage in articulating motion relative to each other. (Wear can also occur on non-articulating surfaces, such as a non-mobile bearing component surface against a tibial tray, or the convex, nonarticulating surface of a liner against the inner diameter of an acetabular cup; the present invention is also applicable to any and all such nonarticulating surfaces.) Additionally, abrasive third body debris, such as bone cement (for example, polymethylmethacrylate ("PMMA") bone cement) and bone debris may migrate to the interface between bearing or articulating surfaces, further accelerating abrasive wear due to so-called three body motion.

Another factor that can influence implant stability and wear is the frictional force generated at the interface between the bearing surfaces. For example, many cases of premature loosening of hip components have been attributed to excessive frictional torque between the femoral head and the acetabular component. Increased friction is also a direct indication of adhesive interaction, or solid—solid contact between bearing surfaces and typically results in increased wear of one, or both bearing surfaces. It is known that increasing the lubricity of the bearing surfaces reduces friction within the artificial joint.

In spite of the increased wear rates, however, mobile bearing joints, such as mobile bearing knee joints, provide a number of advantages over fixed bearing joints. For example, mobile bearing joints provide more natural kinematics and lower stresses at the implant-bone interface. Accordingly, because of the benefits provided, it is important to provide solutions to the increased wear that is generated by mobile bearing joints, even though the present invention is useful for any bearing structure, whether mobile or fixed, articulating or nonarticulating.

Consider the knee. In general, proper knee function such as in walking depends upon the complex interaction and interoperation of a number of bones, ligaments, tendons and cartilage components found in the knee. In particular, condyles forming the distal end of the femur articulate in a hinge-like fashion against the plateau that forms the proximal end of the tibia. A number of ligaments and tendons retain the condyles and tibial plateau in position relative to each other throughout the range of motion, from flexion to extension of the knee. Cartilage components, including meniscal components, are interposed between the condyles and the tibial plateau and thus provide natural bearing surfaces that, among other things, reduce friction and bone wear in the knee. The patella is held in place with tendons and ligaments as it rides in a groove on the anterior surface of the condylar head throughout the range of motion.

In knee joint replacement surgery, a surgeon typically affixes prosthetic components to the patient's bone structure; a first to the patient's femur and a second to the patient's tibia. These components are typically known as the femoral component and the tibial component, respectively. Each component may be formed of a range of subcomponents, such as in a modular fashion. For instance, a tibial tray that corresponds in some ways to the tibial plateau is supported in some prosthetic designs by a cemented or non-cemented tibial stem that is inserted into the canal of the tibia. Similarly, the condylar component can be supported by a stem or other structure that attaches to or inserted into the femur.

The femoral component is placed on a patient's distal femur after appropriate resection. The femoral component is usually metallic, having a highly polished outer condylar articulating surface.

A common type of tibial component uses a tray or plate that generally conforms to the patient's resected proximal tibia. The tibial component also usually includes a stem which extends generally perpendicular to the plate in order to extend into a surgically formed opening in the patient's intramedullary canal.

A healthy knee joint flexes, extends, and rotates as a person walks, sits, bends forward, and climbs stairs. Nature has provided a self-lubricating system of healthy, white cartilage to cover the ends of these bones. It is this smooth, slippery surface that enables the knee to glide like a well-oiled machine with no rough spots to interfere with its precise, rhythmic motion.

In the implant context, this smooth, slippery surface is removed and replaced with a plastic or polymeric (often high density polyethylene ("HDPE") or UHMWPE) insert or bearing. The insert fits between the tibial component and the femoral component and provides a surface against which the femoral component condylar portion articulates.

The bearing may also engage in motion relative to the tibial plate. Such motion can be translational and/or rotational sliding motion relative to the plate. In other types of mobile bearing knee prostheses, the bearing can engage in other types of motion relative to the tibial component and/or femoral component.

As discussed above, one of the problems encountered with mobile bearing systems is the constant wear that occurs between the bearing and the tibial and/or femoral component due to articulation. These problems are, of course, also encountered with other types of artificial joints. The materials currently being used for the frictional surface of most artificial joints include various types of metals, ceramics, and UHMWPE. The wear of UHMWPE inserts or sockets is known to be one of the factors necessitating repeated replacement of artificial joints. The surface of the insert and the surface of the tibial tray are in contact with one another along the substantial range of motion. Additionally, wear particles created by the friction between these materials are suspected as leading to loosening of the prosthesis.

Although not exhaustively, researchers have studied various ways to alleviate or eliminate this wear and/or abrasion. Among others concepts, researchers have attempted to enhance lubrication and alter surface structure of the surfaces that are in sliding or articulating contact. For example, some investigators have attempted to maintain a constant coefficient of friction between two articulating contacting surfaces by using separately-applied lubricants. Such lubricants are commonly solid lubricant films or solid lubricating surfaces. Others have attempted to incorporate a lubricant-type material into the articulating surface itself. In some instances, however, these lubrication models do not work or cannot be tolerated because they introduce undesired contaminants or other undesired physical characteristics into the process of the device.

Additionally, to overcome wear problems associated with artificial joint materials, various surface structures have been studied. For instance, patterns have been introduced in an effort to enhance the lubrication of the joint and reduce the creation of wear particles. See I. Nishimura, et al. "Modification of the Frictional Surfaces of Artificial Joints," *ASAIO Journal,* July–Sept. 1993: M762, which is incorporated herein in its entirety by this reference.

Some references describe experiments conducted with stainless steel ("SUS") surfaces and UHMWPE surfaces having surface patterns. Such surfaces are typically spherical discs of material with a radius of 20 mm. The discs featured a pattern with a diameter from 0.2 to 1.0 mm, a pitch (the distance between each pattern) from 0.6 to 2.0 mm, and a depth of 3 $\mu$m on the SUS surfaces and 1 mm on the UHMWPE surfaces. The application of surface patterns in some instances has been reported to enhance lubrication properties and lower frictional force. Less wear has been found to occur on patterned samples than on samples without a pattern, which was attributed to the ability of the pattern to maintain good lubrication.

For example, the Nishimura reference indicates that a pattern having a diameter of 0.5 mm and a 1.2 mm pitch showed the maximum reduction in frictional force (25%) and the smallest value for UHMWPE wear (8 $\mu$m). When the diameter of the pattern was increased to more than 0.5 mm, the reduction rate decreased and water formation increased. Among other things, this reference fails to discuss the implications that the depth of the pattern has on wear problems, other than fixing the to depth at 3 $\mu$m on SUS surfaces and 1 mm on UHMWPE surfaces. The reference also shows a regular pattern of diameter, pitch and depth used on each surface, without taking various geometries of the pattern, anatomical conditions, or various placement patterns into consideration. These are just a few examples of features that this reference lacks.

There are also patents directed to wear resisting slide members that disclose slide members having circular recessed and projected patterns. The recessed portions are filled with lubricant, and the circular diameter of the recessed portions typically range from 0.2 to 0.8 mm. Circular diameters greater than 0.8 mm cause the area of the projected portions to decrease so that the projected portions cannot support the loads, sliding and lubricating properties are deteriorated due to wear of the slide surface, and unevenness occurs.

Such references also state that the pitch should be in a range of 0.8 to 1.6 mm and that the depth of the recessed portion is set to 1 mm or less, preferably 10 $\mu$m or less. The recessed and projected portions are also arranged regularly over the whole slide surface. Again, among other things, these references fail to suggest that the depths of the recessed portions can be beyond the 1 mm limitation, as well as fail to consider the anatomical properties and various placements of the portions. The area ratio of the recessed portions is also in the range of 30 to 70% with respect to the whole sliding surface. The references also emphasize that if the groove depths are too deep, lubricant is collected in the bottoms of the recessed portions, preventing the lubricant from flowing up to the projected portions, which again emphasizes the minimal depth that is taught, as well as the lubrication aspect, which appears to be the primary benefit provided by the recessed portions.

Various concepts that these references do not consider, however, are that if the recessed portions are not sufficiently deep, synovial fluid may fill the recesses and calcify, essentially re-filling the recesses, thus eliminating the benefits sought to be achieved. Nor do the currently available references consider the benefits of various positionings of the patterns on the surface or the concept of reducing overall areas of wear.

Moreover, other references provide lubricated joints having a fluid filled compartment that can pump fluid into an interarticular gap. The resistance of the fluid to flow is modulated by deforming a glidable, spherical cup, which reduces the gap under higher loads. Grooves may be cut into the cup to concentrate the pressure drop of the fluid flow. Again, these references concentrate on controlling the fluid or lubricant, not on the dimensions of the grooves nor the placement or structure of the grooves.

Various researchers have attempted to improve wear characteristics. For example, they have provided voids on a surface that trap wear particles. Relatively small voids or pockets (microvoids) are incorporated into the microstructure of the material itself. When the surface is in contact with another sliding surface, wear debris generated between the surfaces is trapped in the voids and removed from the interface region. The geometry of the voids is described as generally larger than the dimensions of the wear particles. They are described in the claims as microscopic void regions spaced at microscopic distances from each other.

None of these references described provide the features of the present invention. Among other things, no reference describes a design that considers and optimizes depth, configuration and position of recesses or indentations on a prosthetic implant component bearing surface in a manner that effectively reduces wear of that surface. Nor do the references discuss reducing the area of the bearing surfaces in order to reduce the area of actual contact between articulating surfaces and the benefits that this concept presents. Instead, the references primarily focus on increasing lubrication.

Additionally, the references discussed above do not focus on reduction of area from critical regions where the pressure and wear is particularly high. A reason for this may be that it is counterintuitive to remove material from a support structure in order to strengthen the structure. More particularly, about 85% of wear of mobile bearing knee systems occurs on the underside of the mobile bearing device, with only 15% of wear occurring on the topside. The present inventors have realized that this indicates that there is a greater need to reduce wear on the underside of the device. For example, the wear on a mobile bearing insert underside of a knee replacement system appears to be influenced by the biaxial "cross-shear" motion that is typical in hips, and is thus considered to be more representative of "hip-type" wear. This is contrary to topside wear, which is the traditional "knee-type" wear commonly seen in fixed bearing knees. Similar principles may apply in any number of contexts in any combination of prosthetic implant bearing surfaces, to which the present invention is potentially applicable.

More specifically, a hip is actually a ball and socket-type joint, which interfaces two separate bones—the femur and the pelvis. The pelvis has two cup-shaped depressions, called the acetablua or "sockets." The head of the femur or "ball" fits into the "socket," forming a joint which allows the leg to articulate forward, backward and sideways through a wide, three dimensional, range of motion. The acetabulum is lined with cartilage, which cushions the bones and allows the joint to rotate smoothly and with minimal friction. An envelope of tough ligaments connect the pelvis and femur, covering the joint and stabilizing it. The cartilage also lends strength to the hip joint in order to support the weight of the upper body, and resilience to absorb the impact of exercise and activity. A healthy hip will allow the leg to articulate freely within its range of motion, while supporting the upper body and absorbing the impact that accompanies activities like running and jumping.

During a total hip replacement surgery, damaged and worn parts of the hip are removed and replaced with artificial parts, called prostheses, which will help make the hip strong, stable and flexible again. During surgery, an implant is selected and affixed to the area between the femur and the pelvis. In most cases, the implant will consist of two pieces: a metal stem fitted with a ball at one end ("the head") and a metal or polyethylene cup ("the cup").

The head may be formed of metallic material, polymeric, ceramic or other desired material. It fits into an acetabular cup which has been inserted in the acetabulum of the patient that corresponds to the femur having the femoral implant. The cup may include a liner such as a polymeric liner to receive the head. The liner and metallic cup components may articulate or not relative to each other; the ball articulates relative to the liner. These components replace the socket and ball of the femur to form a new hip joint.

Recent studies conducted on hip replacement systems indicate that the volumetric wear rate of acetabular liners increases with increasing head/cup diameter. See I. C. Clarke, et al., "Hip-Simulator Ranking of Polyethylene Wear—Compassions Between Ceramic Heads of Different Sizes," *Acta. Orthop. Scand.*, 67 (2) (1996): 128–132; W. Sauer, et al., "Predicting the Clinical Wear Performance of Orthopaedic Bearing Surfaces," in J. J. Jacobs and T. L. Craig, eds., *Alternative Bearing Surfaces in Total Joint Replacement; ASTM STP* 1346, December 1998, all of which are incorporated herein by this reference. This is contrary to the general understanding in the field of implant technology, which is that if a force can be spread out over a greater contact area or surface, the stresses experienced are decreased. In other words, by increasing the surface contact area of a support structure, the contact stress is decreased.

On the other hand, the above-described study shows that when a femur head having a large diameter contacts an acetabular liner, the stress and wear generated is increased (even though the stress is "spread out" over a larger area), as compared to that generated when a femur head having a smaller diameter is used. Essentially, increasing the contact surface in this situation increases the wear suffered, rather than decreases the wear. This suggests that the effect of increased wear on increasing total wear volume is stronger than the effect of decreased stresses on decreasing total wear volume for the liner. That is, the increased wear shown suggests that the theory behind "spreading out" contact stress is overshadowed by the fact that increased contact area causes more wear.

Other studies based on theoretical stress analysis have suggested that the head/cup clearance should be as small as possible so that the contact stress and wear rates can be minimized for a given head size. For example, A. Wang et al. have shown that decreasing the head/cup wear area by increasing the radial mismatch between head and cup correspondingly decreased the wear, roughly proportionally to the decreased wear area, despite significantly increased stresses. A. Wang, et al., "Effect of Head/Cup Clearance on the Wear of UHMWPE in Total Hip Replacement," *Trans 24th SFB*, San Diego, Calif., April 1998: 357, which is incorporated herein by this reference. In other words, even if there are additional stresses generated from a less-than-perfect-fit between the head and cup, if contact area is smaller, less wear is seen. This appears to be the case despite the fact that more area is provided for lubrication to flow when a smaller head is used.

The inventors realized that it would be desirable to apply the above-described concepts to various artificial joint prostheses, and applied them to areas of that anatomy that are different in major respects from the hip structure. For example, the concepts that apply to hip-wear may be applied to knee systems and to mobile bearing inserts to reduce wear. It is also desirable to provide reduced wear rates and improved lubrication access through decreasing the wear area of joints in areas that are subjected to high wear, and perhaps even the greatest wear.

For example, although it seems counterintuitive, the inventors realized that it may be desirable to decrease the underside wear or bearing surface area of a mobile bearing insert of a knee joint in order to increase wear resistance. It is also beneficial to be able to reduce wear without the need to apply a separate lubrication or use a material having lubricating-type material incorporated therein, in order to alleviate any additional contaminants or undesired physical complications that may be presented.

It is desirable to provide decreased wear area by providing textured areas that have certain configurations and shapes that have shown to be particularly effective at reducing overall wear rates. For example, it may be desirable to provide sufficiently deep indentations to provide the desired benefits, without canceling those benefits out; that is, to provide recesses sufficiently deep so that lubricating fluids present in the system do not calcify and render benefits provided by the recesses useless.

SUMMARY OF THE INVENTION

The present invention relates to devices for reducing wear in artificial joint systems and medical implant devices, such as knee replacement systems, hip, shoulder, elbow, finger, toe or spinal systems, and the like. One or more of the implant components has at least one textured or patterned bearing surface, the texture or pattern designed and formed in a manner that takes into account depth, pattern and position of the indentations forming the texture or pattern to reduce bearing surface wear.

For example, in one embodiment of the invention, there is provided a mobile bearing knee prosthesis, comprising an insert having an inferior surface adapted to cooperate with a tibial plate and a superior surface adapted to cooperate with a femoral component, the insert having indentations on the inferior surface, whereby the indentations are oriented and dimensioned in a manner that reduces surface area of the insert in contact with the tibial plate, providing lower net wear on the insert as compared to an insert not having such indentations under substantially the same load. In a specific embodiment, the insert is included in a knee replacement prosthesis having a tibial tray, a tibial stem, and a femoral component.

In an alternate embodiment of the invention, there is provided such an insert having indentations covering about 10% to about 20% of the underside surface. In an even more particular embodiment, the indentations range from about 1 mm to about 2 mm deep, from about 1 mm to about 4 mm in pitch, from about 1 mm to about 2.5 mm in diameter, or combinations thereof.

In a counterintuitive recognition and application of clinical findings that have indicated that volumetric wear rate in the hip joint increases by increasing the head size, the inventors have discovered that reducing the bearing surface area by introducing indentations with proper consideration as to depth, pattern, positioning, or combinations thereof should translate to a lower wear rate. They have discovered that reducing the bearing surface area does in fact result in a reduction of volumetric wear, particularly reducing surface area on the underside of a mobile bearing knee insert. Accordingly, the invention seeks to reduce contact area by providing indentations of proper depth, pattern, positioning, or combinations thereof on the bearing surfaces of prosthetic implant components, and particularly by providing such indentations on the inferior (or underside) surface of a mobile bearing insert. Even more particularly, the indentations optimally have a depth between about 1–2 mm and are patterned to reduce the bearing surface area to the greatest extent at regions where maximum wear occurs.

In general, bearing surfaces move relative to each other, whether in articulating or non-articulating motion. This is commonly a source of friction and wear. Articulating motion in most cases creates greater wear; for example, wear testing of a UHMWPE mobile bearing knee with rotation and translation of the mobile bearing insert allowed, indicated that UHMWPE wear rates were about three times higher than those for corresponding fixed bearing knees. Further, it was shown that a greater percentage of the wear occurred on the underside or inferior portion of the mobile bearing insert. (The term "mobile bearing device" or "mobile bearing system" for purpose of this document means any implant device that is subjected to rotational and/or translational movement, whether it be knee, hip, shoulder, elbow, finger, tow, or spinal systems or joints. The terms "underside," "inferior," and "backside" for the purpose of this document mean any portion of an insert that is adapted to contact an upper portion of a component, such as a tibial tray.)

A bearing surface of the present invention is textured, having multiple indentations. The indentations may be provided in any design or pattern or combination of designs or patterns, such as grooves, dimples, straight patterns, straight crossing patterns, curved patterns, curved crossing patterns, holes, channels, slots, or any other geometric design, any of which will collectively be referred to as indentations. The concept is focused on reducing area, not the particular design or pattern used.

These indentations are machined, molded or otherwise provided on the bearing surface, preferably in a manner that reduces bearing surface wear greatest at areas that suffer high wear, or perhaps even the greatest wear, such as certain regions of the underside of a mobile bearing insert. More specifically, because it has been shown that about 85% of the wear suffered by mobile bearing knee systems occurs on the underside of the mobile bearing device, with only 15% of wear occurring on the topside, the indentations are provided on the underside, or the inferior surface, of the device. The described textured or indented surfaces reduce the contact area of articulating components, resulting in wear reduction, less pressure on the joint, and greater lubrication. The actual pattern of indentations is one aspect of this invention, the location of the indentations on the bearing surface is another aspect of the invention, and the geometry of the indentations is a further aspect of this invention.

In the case of a mobile bearing insert, the indentations are preferably located on the underside of the mobile bearing insert, along the surface of the insert that contacts the tibial plate. More particularly, if the insert and tibial plate are allowed to touch and be in direct contact throughout the entire surface, there is about an inch of direct contact. On the other hand, by providing indentations on the surface of the mobile bearing insert that is in contact with the plate, that contact area is reduced. Accordingly, the principles described with respect to reducing hip stress are applicable to reducing knee stress and wear.

Furthermore, the indentations may be of variable shapes and of variable distances from one another. It is not necessary that they span the entire underside, although they may span the entire underside if desired. Particular benefits are derived from their placement at areas of greater wear, however.

The indentations may all be of a constant shape, for example, all circular or all slots, or they may be varied, for example, various shapes on the same surface. The placement or varied patterns may be design dependent, anatomy dependent, wear dependent, or a combination of the above. For example, it may be necessary to maintain certain dimensions of the insert, such as thickness, and the indentations may be placed accordingly.

The indentations may be any suitable size or shape. In a particular embodiment, it has been shown to be particularly beneficial to provide indentations that range from about 1 mm to about 2.5 mm in diameter, about 1 mm to about 4 mm in pitch, and about 1 mm to about 2 mm in depth. Although other dimensions are possible, these have shown to provide particular advantages. Particularly, the depth allows circulation of lubricant, but it not so shallow that lubricant and other fluids calcify or otherwise become lodged in the indentations, effectively blocking the indentations.

It is therefore a feature of the present invention to provide implants that reduce wear.

It is also a feature of the present invention to provide artificial joint implants that reduce wear by reducing bearing surface area, whether of articulating or non-articulating bearing surfaces, from critical regions of such surfaces where wear is great.

It is an additional feature of the present invention to provide mobile bearing surfaces for implants that are textured or that otherwise have indentations, to reduce contact area, thus providing wear reduction.

It is an additional feature of the present invention to provide a bearing surface having a reduced area in which the wear reduction is greater that the surface area reduction.

It is an additional feature of the present invention to provide mobile bearing surfaces that accomplish any or all of the following: reduced surface contact area; smaller contact area in motion; lowered wear of an implant system; greater lubrication.

It is an additional feature of the present invention to provide mobile bearing surfaces for implants that have indentations, textures or recesses, with those portions being located where high wear, perhaps even the greatest wear is experienced.

It is an additional feature of the present invention to provide mobile bearing surfaces for implants that are indented, textured or recessed, with the recessed portions being located on the underside of the mobile bearing insert.

It is an additional feature of the present invention to provide mobile bearing surfaces for implants that are textured or recessed, with the recessed portions being located on the underside of the mobile bearing insert and being located primarily at anterior and/or posterior portions of the mobile bearing insert.

It is an additional feature of the present invention to provide mobile bearing surfaces for implants that have textures or recesses that are about 1–2 mm deep, providing reduced surface area.

It is an additional feature of the present invention to reduce bearing surface wear in prosthetic implants by providing indentations on such surfaces in a manner that takes into account depth, shape, pattern, position, or combinations thereof of the indentations to reduce wear and preferably optimize wear reduction.

Other objects, features and advantages of the present invention will become apparent with respect to the remainder of this document.

DETAILED DESCRIPTION OF THE DRAWINGS

Figure 5:
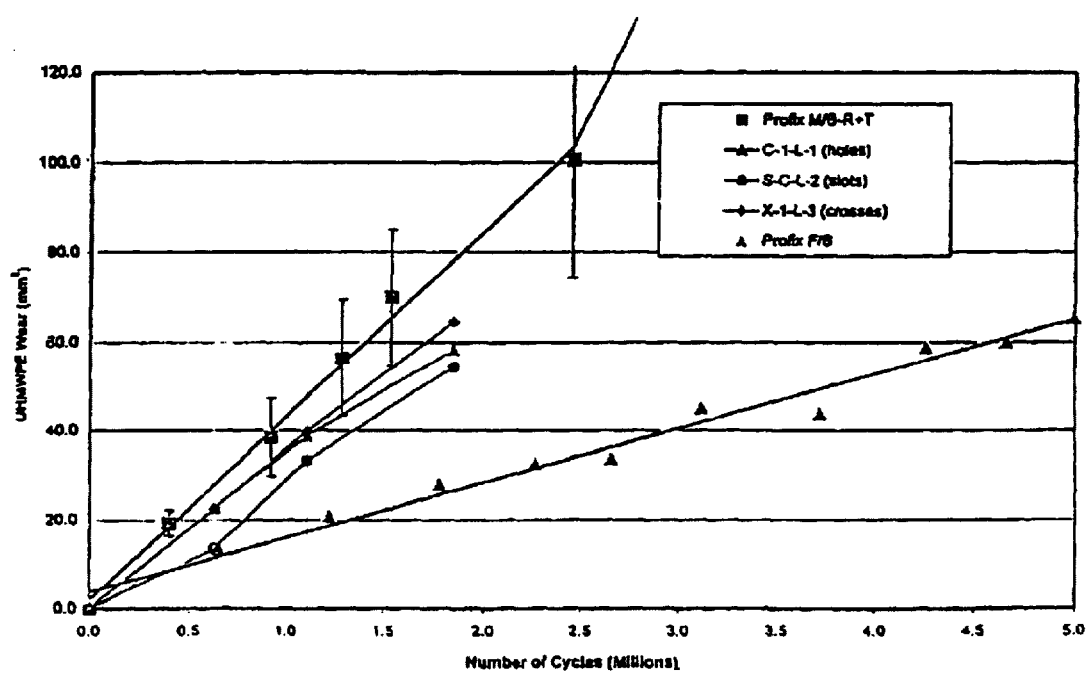
FIG. 5 is a graph showing wear as a function of wear cycles for various indentation conditions compared to baseline mobile bearing and fixed bearing joints.
Figure 6:
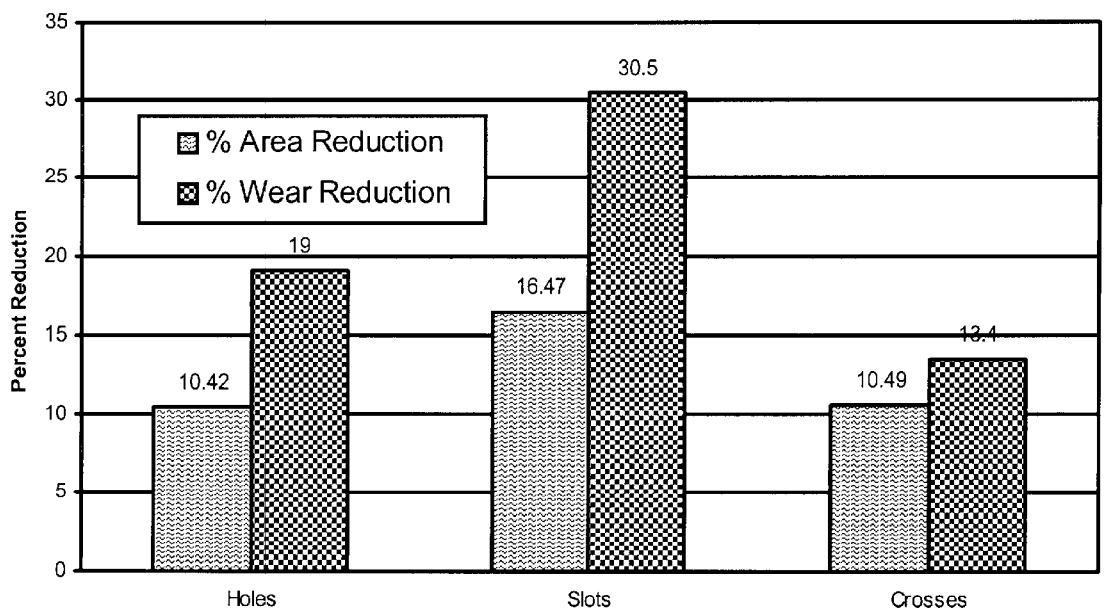
FIG. 6 is a bar graph showing a comparison of reduction in wear as a function of reduction in backside surface area for various tested conditions.
Figure 7:
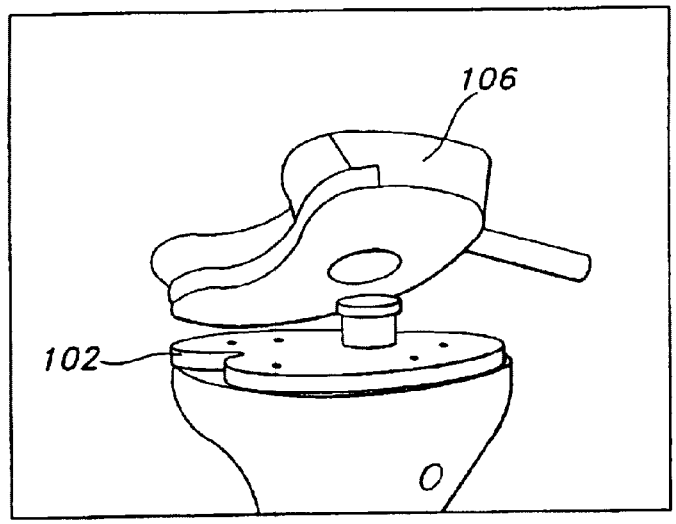
FIGS. 7–9 are perspective views which show portions of a clinical surgical technique that can employ a textured bearing insert according to the present invention.
Figure 8:
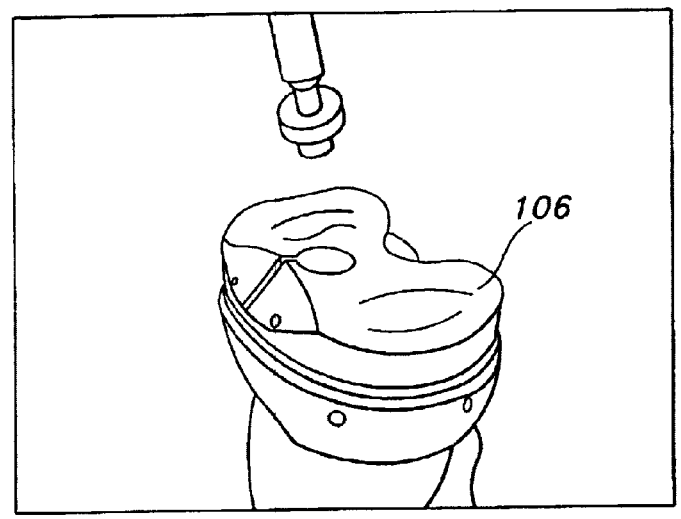
Figure 9:
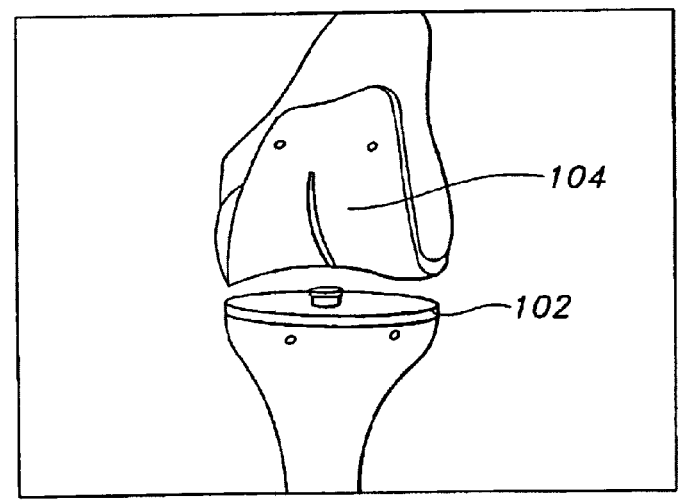

FIGS. 1–4 show various embodiments of mobile bearing inserts according to the present invention. FIGS. 5 and 6 show comparisons between the textured mobile bearing insert of the present invention and those that are currently in use. In order to provide the context in which such inserts are used, FIGS. 7–9 show an implant 100, having a tibial tray 102, a femoral component 104 and a mobile bearing insert 106 (no indentations shown) being implanted. Implant 100 is shown as a total knee replacement system, but may be any type of joint replacement.

In a this type of knee replacement surgery, the surgeon prepares the proximal portion and canal of the femur and tibia in a conventional manner, using broaches, reamers, instruments, and other devices and instruments as desired, to shape the proximal portions of the femur and tibia to a shape and configuration which accepts, as nearly as possible, correctly dimensioned implant components. She then optionally performs trial reduction in order to select the properly configured and sized tibial and femoral implants, and otherwise to gauge dimensions, angles and other parameters that matter in correct installation and implantation, and otherwise to prepare the tibia and femur for the implant.

Once the proper tibial and femoral components are selected, the proximal tibia is prepared and the tibial plate 102 is impacted into the tibia until the distal surface of the plate is flush with the resected tibia. A mobile bearing insert 106 is then placed on the tibial base plate 102 and secured using an optional rotation peg with a torque wrench (not shown). In the preferred embodiment, approximately 75 inch pounds of torque is used to secure the rotation peg, but that may vary depending upon the prescribed clinical technique. Once the femoral component is similarly placed in the patient, the knee structure is repositioned and the surgery completed.

Referring back to FIG. 1, a mobile bearing insert 10 having anterior portion 12, posterior portion 14, medial portion 13, and lateral portion 15 is shown. Indentations 16 in the shape of curves are shown, primarily located at the anterior and posterior portions. Indentations 16 are shaped irregularly, i.e., they are not perfectly circular. This embodiment is labeled as "Slots" (or condition S) in FIGS. 5 and 6 and throughout this specification.

Figure 2:
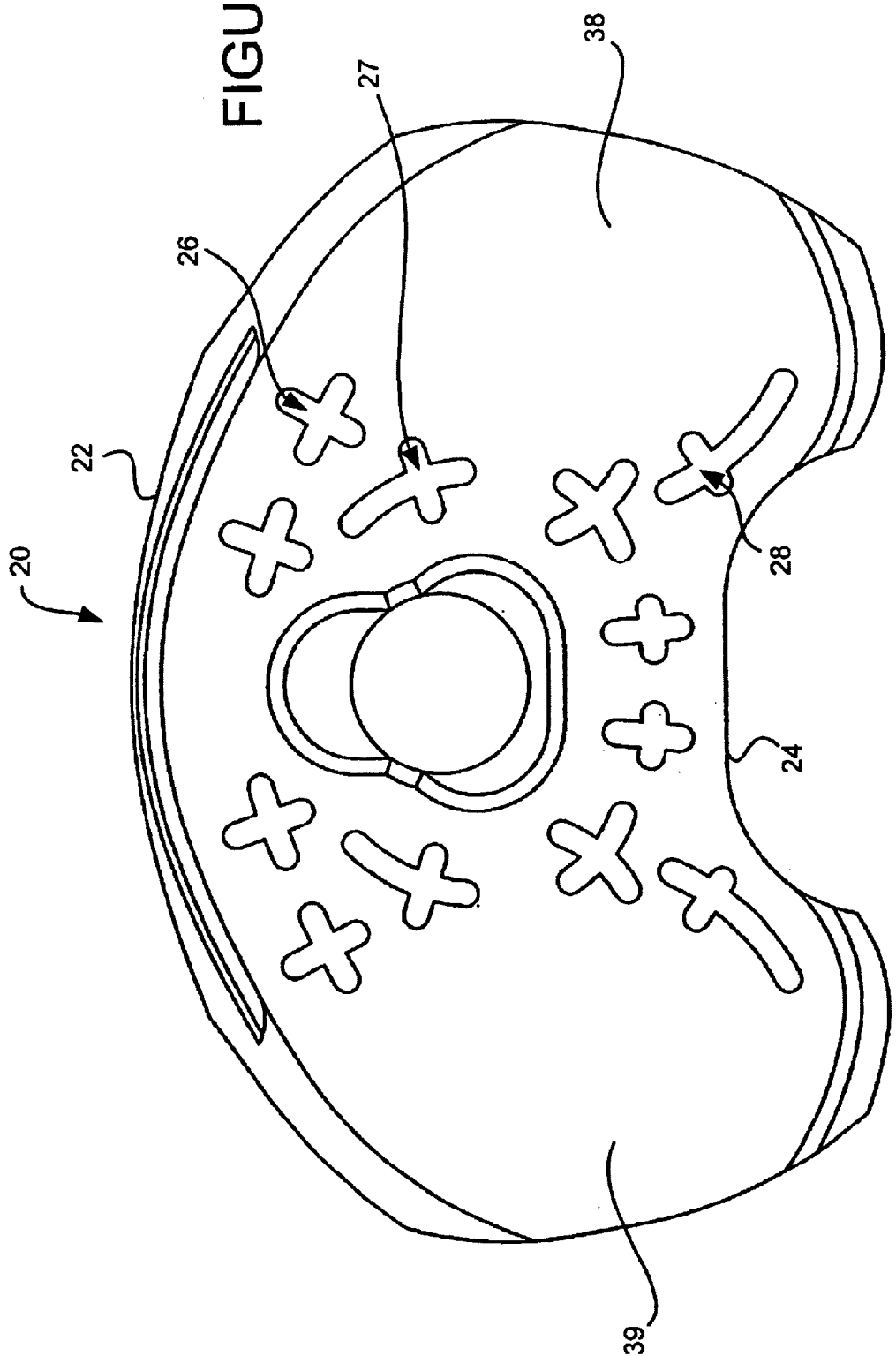
FIG. 2 is a bottom plan view of a second embodiment of a mobile bearing insert according to the present invention.

FIG. 2 shows a mobile bearing insert 20 having anterior portion 22 and posterior portion 24. Indentations 26 in the shape of crosses are shown, primarily located at the anterior and posterior portions. Indentations 26 are shaped irregularly, i.e., they are not perfectly circular nor are they necessarily smooth in border. This embodiment is labeled as "Crosses" (or condition X) in FIGS. 5 and 6 and throughout this specification.

Figure 3:
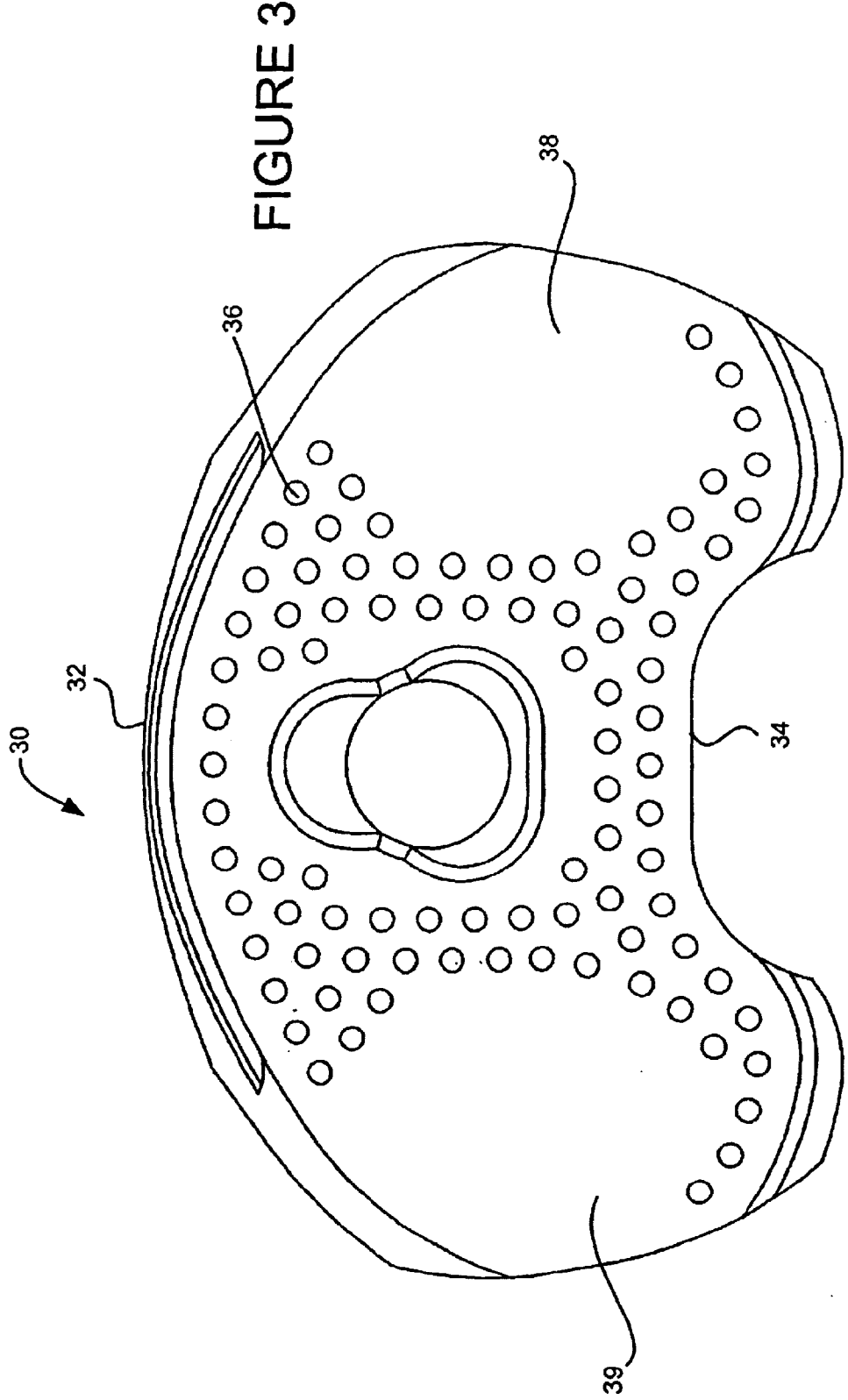
FIG. 3 is a bottom plan view of a third embodiment of a mobile bearing insert according to the present invention.

FIG. 3 shows a mobile bearing insert 30 having anterior portion 32 and posterior portion 34. Indentations 36 in the shape of small circles are shown, primarily located at the anterior and posterior portions, and extending to the ends of posterior portion 34. This embodiment is labeled as "Holes" (or condition C) in FIGS. 5 and 6 and throughout this specification. Although the holes are shown in FIG. 3 as primarily perfectly circular, it is understood that perfect symmetry is not required for holes to fall within the spirit of this invention.

These various embodiments focus the placement of indentations 16, 26 and 36 at areas of particular wear and also at areas that enhance design and take in to account design constraints. For example, areas 38 and 39 are opposite of where the femoral component articulates against the topside (not shown) of insert 30, which does not necessarily have indentations. By providing strategic placement of indentations 36, the thickness of the insert 30 can be maintained at certain areas while still providing reduced area at desired locations. In this embodiment, the desired locations are shown to be anterior 32 and posterior 34 portions.

Figure 4:
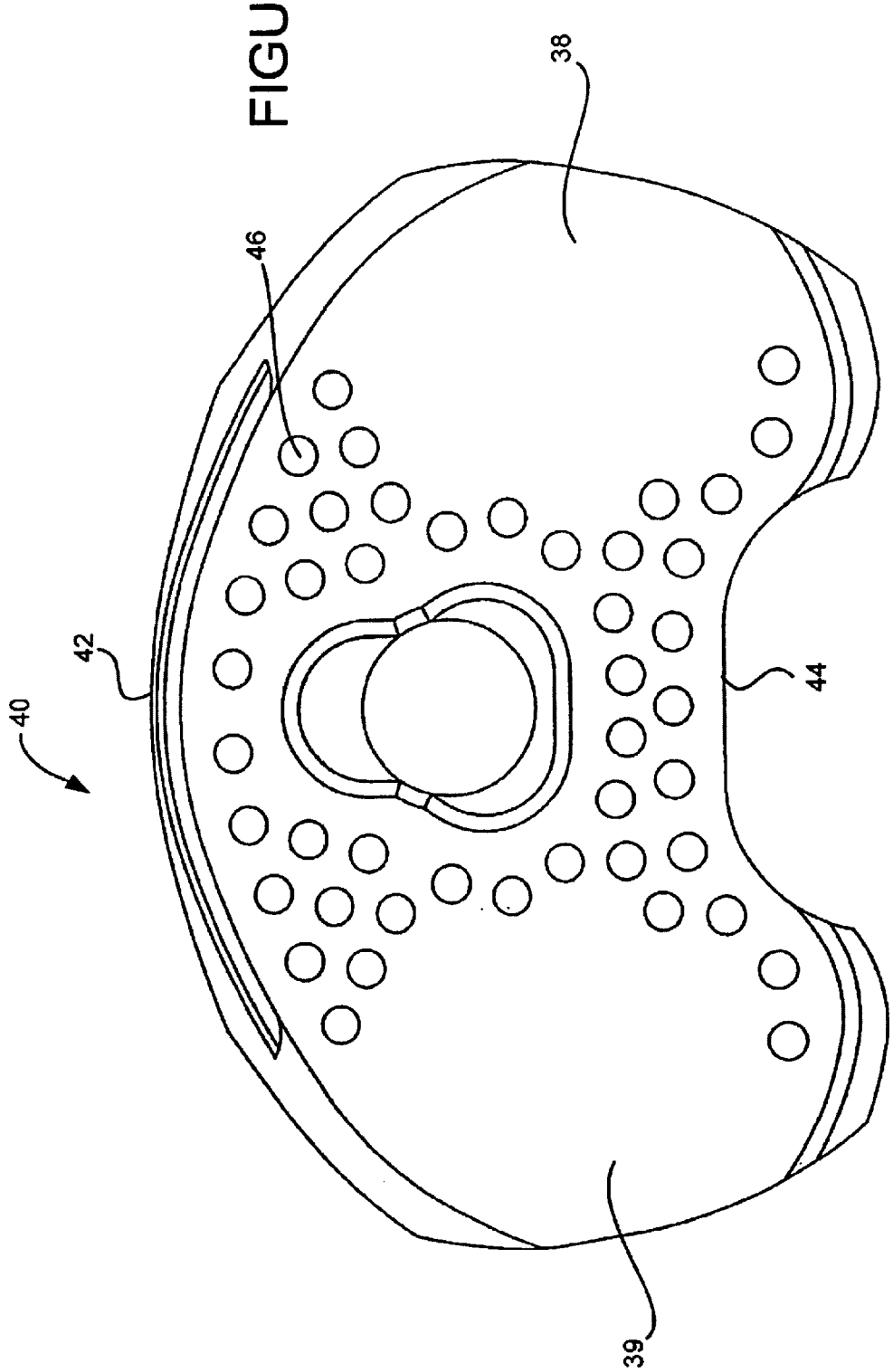
FIG. 4 is a bottom plan view of a forth embodiment of a mobile bearing insert according to the present invention.

FIG. 4 shows a mobile bearing insert 40 having an anterior portion 42 and a posterior portion 44. Indentations 46 are in the shape of circles larger than those shown in FIG. 3, primarily located at the anterior and posterior portions, and extending to the ends of posterior portion 34. This embodiment also provides the above-described advantages. It is also labeled as "Holes" (or condition H) in FIGS. 5 and 6 and throughout this specification, and is included to demonstrate that the particular sizes shown in any of FIGS. 1–4 are provided for exemplary purposes only and are not intended to limit to concepts disclosed by this invention.

FIGS. 1–4 show indentations 16, 26, 36, and 46 located at anterior and posterior ends. As discussed, these areas tend to show high wear, perhaps even the greatest wear in mobile bearing knee implants. Accordingly, this placement in concentrated regions of high wear helps provide the desired benefits discovered by the present inventors. However, the location of the machined patterns or indentations is not required to be concentrated in any one area, and only one embodiment of the invention is shown. For example, in an alternate embodiment, indentations may extend across the entire surface of mobile bearing inserts 10, 20, 30, and 40.

Figure 1:
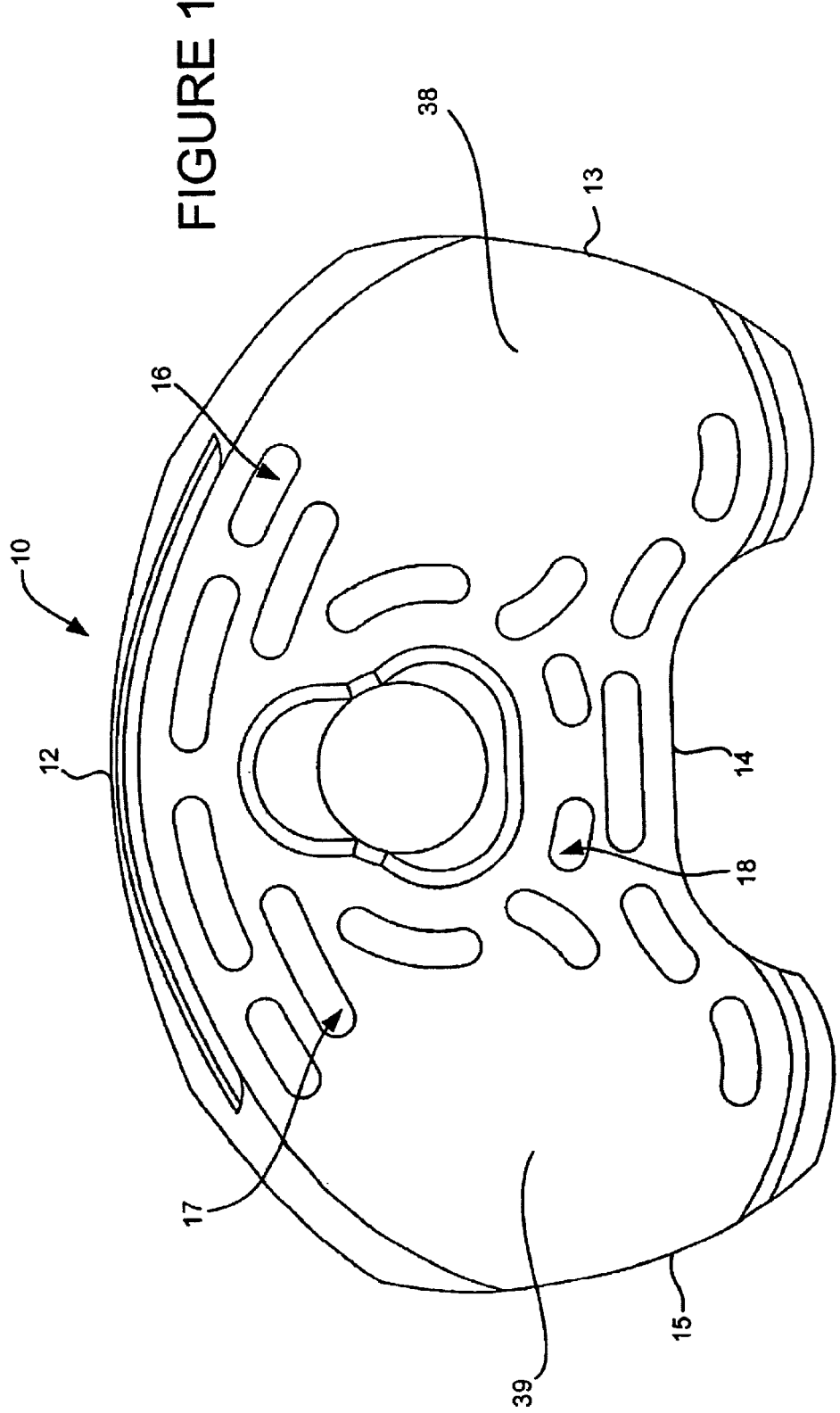
FIG. 1 is a bottom plan view of a first embodiment of a mobile bearing insert according to the present invention.

Further, FIGS. 1–4 show that the indentations can vary in diameter and pitch. In other words, indentation 16 in FIG. 1 is a different shape and size than indentation 17 of FIG. 1, which is also a different shape and size than indentation 18 of FIG. 1. Indentations 16, 17 and 18 are also different distances from one another. Although FIGS. 3 and 4 do not show this varied nature, it is possible for them to have various combinations of diameter and pitch as well.

Indentations may also, but need not be, oriented at angles. For example, FIG. 2 shows indentations 26, 27, and 28 all on different axes.

FIG. 5 graphically illustrates wear cycles resulting from the testing of the present invention. Mobile bearing knees without textured surfaces showed the highest wear rates and fixed bearing knees showed the lowest wear rates. Because of the benefits that are achieved with mobile bearing knees, it is desirable to provide a mechanism that can reduce the high wear exhibited. Three embodiments were tested, although these embodiments are clearly not the only embodiments encompassed by this invention. First, the embodiment with crosses, shown in FIG. 1, presented the greatest wear reduction compared to mobile bearing knees without indentations. FIG. 5 also shows that the hole and cross embodiments also lowered wear rates.

FIG. 6 shows a bar graph representing backside (or underside) wear area reduction. This graph shows that the actual reduction in wear is greater than the area removed. The backside (or underside) has indentations covering about 10 to about 20% of the surface area of the underside of the component, particularly 10.42–16.47%. The wear reduction obtained was between about 10% to about 35%, and particularly between about 13.4% and about 30.5%. The greatest amount of wear reduction obtained was 30.5%, although this is not intended to be upper cut-off level by any means. It should be understood that these figures are provided as an example only. Higher or lower wear reduction may be obtained in accordance with various embodiments of this invention.

Mobile bearing inserts according to the present invention may also be used for other prostheses, including hip, shoulder, elbow, finger, toe or spinal systems. There may particular use in the field of shoulder implants and acetabular cups for reducing wear area, for reducing stresses, and/or for providing increased lubrication.

One advantage which can be provided by this invention is that indentations can be located in areas of greatest wear. For example, indentations can be on the underside of a mobile bearing insert and/or where there appears to be the most wear on the insert. Furthermore, another advantage is that the indentations are about 1 mm to 2 mm deep to provide reduced surface area and thus reduced wear, but are also deep enough so that fluids do not calcify or clog or otherwise block the indentations.

The mobile bearing inserts of this invention may be formed of any desired material, such as UHMWPE, Teflon, or any desired grade plastic material. The chief aim of mobile bearing inserts 10, 20, 30, and 40 and other mobile bearing inserts according to the present invention can therefore be seen to provide reduced area so that there is reduced wear. So long as that result is obtained, any structure which functions in any way to accomplish such reduced wear is within the scope of the present invention. As stated above, the mobile bearing insert can also, but need not, accomplish other results such as improved lubrication and reduced stress.

In the embodiments shown, the pattern of indentation on the underside of the bearing insert surface is configured so that there are no indentations in the areas with direct loads that are imposed by the condylar surface onto the tibial tray. In other words, there are no indentations that reduce the volume of material that resists those loads. For design reasons, it may not be desirable to remove area from such locations because of, for example, minimum thickness standards or load bearing considerations. As a consequence, material is not removed from the areas that would intuitively exhibit the most wear, yet, reduced wear area is still shown when other areas are reduced.

Put another way, it is not critical for the indentations to be located at an area or a point where the bearing component is required to resist the point loads. The advantage of reduced wear is still provided if area is reduced in areas of high wear, even if they are not the areas of the absolute highest wear.

On the other hand, there may be a possibility that wear occurs paradoxically at places where the point loads are not the greatest, so that wear is reduced without negatively creating excess deformation of the component by reducing surface area at places where point loads are. The bearing plate is not shown textured at places where there are heavy point loads from the condyle, but the indentations do not need to be located right at the areas of greatest wear in order to reduce a great amount of wear because much wear occurs paradoxically at a place where there are no point loads or where point loads are minimal. Essentially, it is possible to reduce surface area where there are no point loads, but where wear is still exhibited, in order to reduce wear from the component.

If the indentations can be located, placed, and configured in a way that emphasizes, focuses, and leverages on depth pattern and positioning, wear area can be reduced. It is not necessary to place indentations at regions with point loads in order to receive the described benefits. There is still a great amount of wear produced on other areas of the insert. Wear is also produced, paradoxically, in areas where there are no point loads and there does not need to be a lot of volume of the material to resist the point loads in order to release deformation.

The following example describes in more detail the testing and concepts involved in one embodiment of the present invention.

EXAMPLE

Standard mobile bearing inserts (MBK-1) with various underside reduced-area patterns were prepared. The selection of patterns was based on the following criteria:
  machining feasibility;
  maximum removal of material with minimum effect on integrity;
  maintain a minimum distance between holes or slots;
  remove no more than 2 mm depth of material; and
  avoid holes or slots within 2 mm of edge or directly under center of tibial plateaus (to maintain 6 mm thickness).
Although the patterns were selected using the above criteria, the listed criteria is not critical, and any other possible patterns that could have been chosen are within the spirit and scope of this invention. As discussed, the primary goal is to reduce surface area.

Patterns with crosses (X), slots (S), and holes (C), and were conceived and are shown in FIGS. 1–4. The proportions shown are relatively accurate to those used, although they may be varied in actual practice as necessary. The reduction in underside area for each of these surfaces is summarized below in Table 1.

Femoral components and mobile bearing tibial platforms were used, and wear testing was conducted according to current protocol. The tests conducted were identical to those used for the mobile bearing and fixed bearing baseline tests. Pertinent parameters are shown below:
  Frequency: 1 Hz;
  Lubricant: 50% defined serum (diluted with deionized water);
  Abrasive: none;
  Activity inputs: combined walking (TKR with 10° rotation) and stair climbing (10,000 walk: 1000 stair);
  Duration: 1,844,622 cycles (3 wear measurements).
All curve-fitting of wear data for this study was conducted by linear regression.

Wear data for the test run with reduced underside area mobile bearing inserts are listed below in Tables 1 and 2.

TABLE 1

Underside Wear Area Analysis

| Condition | Underside Surface Area (in$^2$) | Surface Area Reduction | Wear Reduction |
|---|---|---|---|
| Standard Insert | 2.997 | | |
| C | 2.685 | 10.42% | 19.0% |
| S | 2.504 | 16.47% | 30.5% |
| X | 2.683 | 10.49% | 13.4% |

TABLE 2

Cumulative Volumetric. Wear (mm$^3$) vs. Cycles for Test reduced underside area

| | UHMWPE Wear (mm$^3$) | | |
|---|---|---|---|
| Cycles | C | S | X |
| 623,336 | 22.6 | 13.4 | 22.6 |
| 1,103,586 | 38.7 | 33.2 | 39.8 |
| 1,844,622 | 58.3 | 54.4 | 64.5 |
| Wear per million cycles (mm$^3$) by linear regression | 33.2 | 28.5 | 35.5 |

Individual wear data are shown graphically in FIG. 5. Group wear data for baseline mobile bearing and fixed bearing tests are included for comparison. The mean linear wear rate for the baseline mobile bearing condition was 41.0±10.7 mm$^3$/106 cycles. In comparison, condition C exhibited a 19.0% lower wear rate (33.2 mm$^3$/10$^6$ cycles), condition S exhibited a 30.5% lower wear rate (28.5 mm$^3$/10$^6$, and condition X exhibited a 13.4% lower wear rate (35.5 mm$^3$/10$^6$). These statistics are mere examples of results that can be achieved applying the concepts embodied in this application.

It is worthy to note that wear rate reductions are all 1.3 to 1.8 times the surface area reduction (Table 1, also shown graphically in FIG. 6). The greatest wear rate reduction correlates with the greatest surface area reduction (condition S).

The first observation of the tibial insert undersides (623, 336 cycles) revealed the normal location and coverage (60–70%) of initial wear. This initial wear location was on the posterior half (greater toward the posterior edge) and at the anterior edge of the underside surface. The subsequent observations indicated that the unworn regions were gradually filling in, but it appeared that the regions with initial wear were probably still wearing at a higher rate. This is likely due to the combination of femoral-tibial contact location during peak loading (posterior), the probable rocking that occurs at the unconstrained tibial insert/tibia platform interface, and the magnification of motions that occur farthest from the center of rotation.

This non-uniform wear distribution is significant considering the nominally flat-on-flat contact at this interface. The presence of holes and slots appeared to have little or no influence on the wear features and patterns. Additionally, frontside wear appeared to be relatively mild as has been found previously.

The location of the machined patterns does not have to be concentrated in a particularly greater or lesser wear area overall (if anything, they were slightly more concentrated in greater wear areas). Thus, the result that the wear reductions were 1.3 to 1.8 times greater than the surface area reductions suggests that the holes and slots may have been providing improved lubricant access which further reduced wear. With the patterns evaluated in this study, no visual deformation or loss of integrity due to the machined patterns was detected following 1.84 million cycles of wear testing. An attempt at conducting dimensional analyses (by Coordinate Measurement Machine or "CMM") of the holes and slots, before and after testing, was initiated but not successfully completed.

Finally, the incidence and effect of CoCr tibial platform scratches on tibial underside wear was also noted. At the first observation (623,336 cycles), typical AP-oriented scratches were observed in all three tests. The tibial platform mated with condition S exhibited the fewest scratches at this point and there was correspondingly 41% less UHMWPE for this condition than the other two. By the end of the test (1,844,622 cycles), tibial platform scratches were fairly similar, possibly greater for condition X. Consistent with this, the wear for condition S became more similar to the other two—16% less than Y and 7% less than C. It was noted that tibial scratches in this series appeared somewhat milder than in previous series, accounting for the difference in duration.

In summary, the reduced-area patterns machined into the mobile bearing tibial insert underside surfaces resulted in reductions in wear rates from 13.4% to 30.5%. This is believed to be primarily a result of the direct reduction of wear area, but other factors such as improved lubricant access (also a result of the machined patterns) and milder tibial platform scratches (an uncontrolled variable) may have also played a role.

While any of the three machined patterns tested and specifically described appear to be promising, condition S (slots) may be preferred. The positioning and coverage of these patterns could be further optimized to address the highest wear regions. Moreover, it was found that tibial platform scratches may have some influence on tibial underside wear. Researchers are conducting an ongoing study to try to identify the cause(s) of these scratches.

The disclosure of devices and processes as recited above is not intended to limit the scope of the present invention. It provides more broadly for artificial joint components to slide without creating advanced stages of wear. Various sizes, geometries, and placements of indentations may be used in order to offer optimal wear reduction. In particular, designs that reduce subsurface stress by decreasing contact area of articulation rather than increasing it can be considered to fall within the scope of this invention.

The foregoing description of the preferred embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

What is claimed is:

1. A mobile bearing knee implant, comprising:
   an insert having (a) an inferior surface adapted to cooperate with a tibial plate, wherein the inferior surface has an anterior portion, a posterior portion, a medial portion, and a lateral portion and (b) a superior surface adapted to cooperate with a femoral component, the insert having indentations on the inferior surface primarily located at or near the anterior and posterior portions of the inferior surface, whereby the indentations are oriented and dimensioned in a manner that reduces surface area of the insert in contact with the tibial plate, providing lower net wear on the insert as compared to an insert not having such indentations under substantially the same load.

2. The mobile bearing knee implant of claim 1, wherein the location of indentations on the inferior surface is generally opposite the corresponding locations at which the femoral component articulates on the superior surface.

3. The mobile bearing knee implant of claim 1, wherein the indentations are positioned such that they reduce contact surface at areas at which the insert experiences high levels of wear in use.

4. The mobile bearing knee implant of claim 1, wherein the indentations cover from about 10% to about 20% of the surface area of the inferior surface.

5. The mobile bearing knee implant of claim 1, wherein the indentations reduce typical wear of the insert by about 10% to about 35%.

6. The mobile bearing knee implant of claim 1, wherein the indentations are of a shape selected from the group consisting of grooves, dimples, straight patterns, straight crossing patterns, curved patterns, curved crossing patterns, holes, channels, and slots.

7. The mobile bearing knee implant of claim 1, wherein the indentations are of a generally constant shape.

8. The mobile bearing knee implant of claim 1, wherein the indentations are of varied shapes.

9. The mobile bearing knee implant of claim 1, wherein the indentations are of a sufficient depth to allow circulation of lubricant but to prevent fluids or wear debris or from calcifying in or blocking the indentations.

10. The mobile bearing knee implant of claim 1, wherein the indentations range from about 1 mm to about 2 mm deep.

11. The mobile bearing knee implant of claim 1, wherein the indentations range from about 1 mm to about 4 mm in pitch.

12. The mobile bearing knee implant of claim 1, wherein the indentations range from about 1 mm to about 2.5 mm in diameter.

13. A prosthesis adapted for use with a tibial tray and femoral component, comprising:
   (a) a mobile bearing insert having an upper and a lower surface,
   (b) the lower surface having indentations covering about 10% about 20% of the surface area of the lower surface of the component, the indentations positioned on the lower surface opposed to the corresponding locations on the upper surface at which the upper surface would articulate with a femoral component and primarily located at or near the anterior and posterior portions of the lower surface and dimensioned in a manner that reduces the surface area of the lower surface, wherein when the lower surface is in contact with the tibial tray, the mobile bearing insert experiences lower net wear as compared to an insert not having such indentations under substantially the same load.

14. The prosthesis of claim 13, wherein the component is a mobile bearing insert comprising ultra high molecular weight polyethylene.

15. The prosthesis of claim 14, wherein the mobile bearing insert is for use in a mobile bearing knee, the prosthesis further comprising a tibial stem, a tibial tray, and a femoral component.

16. A knee replacement prosthesis, comprising:
(a) a tibial tray;
(b) a tibial stem;
(c) a femoral component; and
(d) a mobile bearing insert comprising an inferior surface adapted to cooperate with the tibial plate, the inferior surface having an anterior portion, a posterior portion, a medial portion, and a lateral portion, and a superior surface adapted to cooperate with the femoral component, the insert having indentations on the inferior surface primarily located at or near the anterior and posterior portions of the inferior surface, whereby the indentations are oriented and dimensioned in a manner that reduces surface area of the insert in contact with the tibial plate, providing lower net wear on the insert as compared to an insert not having such indentations under substantially the same load.

17. A mobile bearing device, comprising:
a mobile bearing insert having an underside surface adapted to cooperate with a first component and a topside surface adapted to cooperate a second component, the insert having a pattern of indentations on its underside surface that are oriented and dimensioned on the underside surface generally opposite the corresponding locations on the topside surface where the upper surface would articulate with a femoral component, the indentations being primarily located at or near the anterior and posterior portions of the underside surface and covering about 10% to about 20% of the underside surface.

18. A mobile bearing prosthesis, comprising:
an insert having surfaces adapted to cooperate with additional components, the insert having indentations covering about 10% to about 20% of whichever surface experiences higher wear in use, whereby the indentations act to reduce wear, the indentations primarily located at or near anterior and posterior portions of the insert and having one or more of the following features:
(i) ranging from about 1 mm to about 2 mm deep;
(ii) ranging from about 1 mm to about 4 mm in pitch; and
(iii) ranging from about 1 mm to about 2.5 mm in diameter.

19. The mobile bearing prosthesis of claim 18, wherein the indentations have at least two of the features (i), (ii), and (iii).

20. The mobile bearing prosthesis of claim 18, wherein the indentations have all three features (i)–(iii).

21. The mobile bearing prosthesis of claim 18, further comprising a tibial stem, a tibial tray, and a femoral component.

* * * * *